(12) United States Patent
Landau et al.

(10) Patent No.: US 6,935,384 B2
(45) Date of Patent: Aug. 30, 2005

(54) NEEDLE-FREE INJECTION SYSTEM

(75) Inventors: Sergio Landau, Laguna Niguel, CA (US); John R. Marshall, Beaverton, OR (US)

(73) Assignee: Bioject Inc., Tualatin, OR (US)

( * ) Notice: Subject to any disclaimer, the term of this patent is extended or adjusted under 35 U.S.C. 154(b) by 111 days.

(21) Appl. No.: 10/370,029

(22) Filed: Feb. 19, 2003

(65) Prior Publication Data

US 2004/0159364 A1 Aug. 19, 2004

(51) Int. Cl.⁷ .............................................. B65B 1/04
(52) U.S. Cl. ................................ 141/2; 141/9; 141/27; 141/129
(58) Field of Search .......................... 141/2, 9, 18, 27, 141/100, 129, 258, 312, 319, 357, 383, 384; 604/614, 82, 201, 244

(56) References Cited

U.S. PATENT DOCUMENTS

| | | |
|---|---|---|
| 2,653,604 A | 9/1953 | Hein, Jr. |
| 2,655,604 A | 10/1953 | Hütter |
| 2,680,439 A | 6/1954 | Sutermeister |
| 3,734,147 A * | 5/1973 | Borutta et al. ................. 141/27 |
| 3,807,464 A * | 4/1974 | Pitesky ........................ 141/97 |
| 4,335,760 A * | 6/1982 | Kabadi et al. ............... 141/129 |
| D277,506 S | 2/1985 | Ibis |
| 4,596,556 A | 6/1986 | Morrow et al. |
| 4,739,973 A | 4/1988 | Herndon |
| 4,790,824 A | 12/1988 | Morrow et al. |
| 4,940,460 A | 7/1990 | Casey, I. et al. |
| 4,941,880 A | 7/1990 | Burns |
| 4,966,581 A | 10/1990 | Landau |
| 5,064,413 A | 11/1991 | McKinnon et al. |
| 5,312,335 A | 5/1994 | McKinnon et al. |
| 5,312,577 A | 5/1994 | Peterson et al. |
| D349,958 S | 8/1994 | Hollis et al. |
| 5,383,851 A | 1/1995 | McKinnon, Jr. et al. |
| 5,399,163 A | 3/1995 | Peterson et al. |
| 5,466,220 A | 11/1995 | Brenneman |
| 5,503,627 A | 4/1996 | McKinnon et al. |
| 5,520,639 A | 5/1996 | Peterson et al. |
| 5,649,912 A | 7/1997 | Peterson |
| 5,746,714 A | 5/1998 | Salo et al. |
| 5,782,802 A | 7/1998 | Landau |
| D399,951 S | 10/1998 | Drach |
| 5,840,061 A | 11/1998 | Menne et al. |
| 5,879,327 A | 3/1999 | Moreau DeFarges et al. |
| 5,891,086 A | 4/1999 | Weston |
| 5,893,397 A | 4/1999 | Peterson et al. |
| 5,993,412 A | 11/1999 | Deily et al. |
| 6,096,002 A | 8/2000 | Landau |
| 6,132,395 A | 10/2000 | Landau et al. |
| 6,174,304 B1 * | 1/2001 | Weston ........................ 604/414 |
| 6,223,786 B1 * | 5/2001 | Castellano ..................... 141/2 |
| 6,264,629 B1 | 7/2001 | Landau |
| 6,302,160 B2 * | 10/2001 | Castellano ..................... 141/9 |
| 6,319,224 B1 | 11/2001 | Stout et al. |
| 6,383,168 B1 | 5/2002 | Landau et al. |
| 6,471,669 B2 | 10/2002 | Landau |
| 6,506,177 B2 | 1/2003 | Landau |
| 6,544,084 B1 | 4/2003 | Nanami |
| 6,572,581 B1 | 6/2003 | Landau |
| 6,585,685 B2 | 7/2003 | Staylor et al. |
| 6,602,222 B1 | 8/2003 | Roser |
| 6,607,510 B2 | 8/2003 | Landau |
| 6,610,042 B2 | 8/2003 | Leon et al. |
| 2002/0087117 A1 | 7/2002 | Stout et al. |
| 2002/0123717 A1 | 9/2002 | Landau |
| 2002/0123718 A1 | 9/2002 | Landau |
| 2003/0065286 A1 | 4/2003 | Landau |
| 2003/0093030 A1 | 5/2003 | Landau |

* cited by examiner

Primary Examiner—Khoa D. Huynh
(74) Attorney, Agent, or Firm—Kolisch Hartwell, P.C.

(57) ABSTRACT

A method and apparatus for providing high throughput injections is provided. The invention provides a filling device adapted to deliver injectate from a common reservoir to a plurality of disposable fluid injection assemblies and a reusable propulsion assembly adapted to receive a filled disposable fluid injection assembly and deliver an injection to a patient.

27 Claims, 6 Drawing Sheets

NEEDLE-FREE INJECTION SYSTEM

BACKGROUND OF THE INVENTION

It is often desirable to deliver inoculations, medications, or other injectable substances to a large number of recipients. For example, it has been shown that vaccinations are an effective method for reducing and/or eliminating the spread of communicable diseases. However, the delivery of injections to large numbers of people presents several problems including expense, difficulty of transportation, cross-contamination between recipients, and the creation of hazardous biowaste. These problems can be compounded in economically deprived areas where resources may be limited.

Current methods for delivering vaccinations to populations of recipients typically use needled syringes. These methods typically require filling of the syringes and disposal of the needle and syringe after each use. Even in the hands of the most careful users, accidental needle sticks, and the accompanying concerns about cross-contamination take place.

Needle-free injection systems allow a faster immunization process than needled syringes and eliminate the possibility of accidental needle sticks. However, because the nozzle of the needle-free injector (rather than a disposable needle) makes contact with the patient during injection, the use of current needle-free injection systems to inject multiple patients raise concerns about contamination unless the equipment is properly sterilized between injections. Therefore, it is important that equipment is properly sterilized between injections. However, this can increase costs and reduce the number of injections that can be administered in a given time period, decreasing the likelihood that everyone who needs or wants a vaccination will receive one.

SUMMARY OF THE INVENTION

In one embodiment, the present invention provides a needle free injection system including an injection assembly and a filling device. The injection assembly may include a single-use fluid ejection assembly and a propulsion assembly. The single-use injection assembly may include a body terminating in a nozzle, a fluid reservoir housed within the body, and a plunger disposed within the fluid reservoir. The propulsion assembly may include a housing adapted to receive at least a portion of the removable fluid ejection assembly and a propulsion system adapted to apply sufficient force to the fluid ejection assembly to cause ejection of the fluid injectate through the nozzle. The filling assembly may be adapted to sterilely deliver a predetermined amount of injectate from a common reservoir to a plurality of fluid ejection assemblies.

DETAILED DESCRIPTION OF A PREFERRED EMBODIMENT OF THE INVENTION

Figure 1:
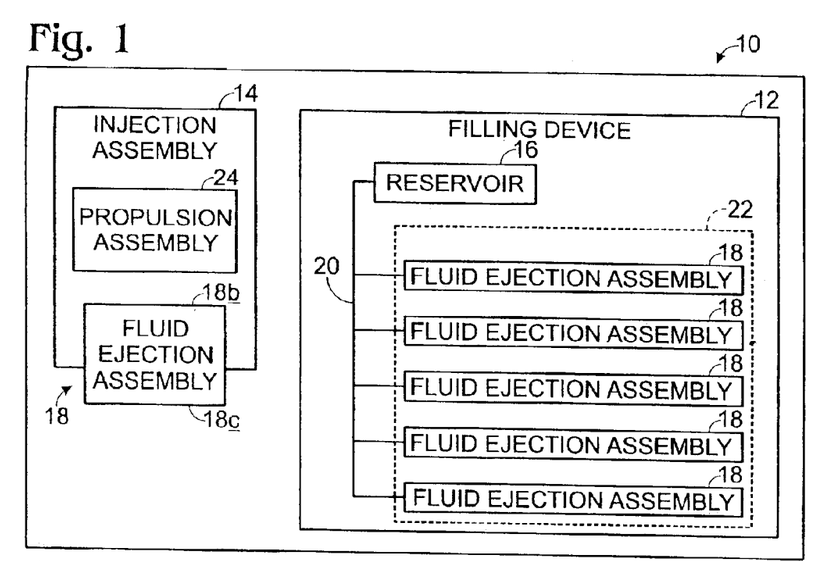
FIG. 1 is a block diagram of a high throughput needle-free injection system according to the present invention.

In one embodiment the invention provides a high throughput needle-free injection system. As shown, system 10 may include a filling device 12 and a needle-free injection assembly 14. Filling device 12 is adapted to sterilely transfer a predetermined amount of injectate from a reservoir 16 to a plurality of fluid ejection assemblies 18 via a fluid path 20. As shown, a carrier 22 may hold or otherwise join two or more of the fluid ejection assemblies 18 together. In some embodiments, all components of the filling device that come into contact with the injectate, including the reservoir, fluid path, and fluid ejection assemblies may be disposable. Some components, such as the reservoir or fluid ejection assemblies may be single-use, such that once their contents are depleted they are thrown away. Other components, such as the fluid path, may be used for a given period of time, such as a day, or for a certain number of uses, such as for 100 cartridge fillings, and then disposed of.

Needle-free injection assembly 14 includes a propulsion assembly 24 and may removably engage a filled fluid ejection assembly 18. Upon activation by a user, injection assembly 14 may eject the contents of the fluid ejection assembly 18 with sufficient velocity to deliver the injectate to a desired target, such as beneath the dermal layers of a recipient.

Typically, a new fluid ejection assembly 18 is inserted into needle-free injection assembly 14 before each injection. As shown, the fluid ejection assembly 18 may be seated within needle-free injection assembly 14. Fluid ejection assembly 18 may include a first portion 18b that is inserted into needle-free injection assembly 14 and a second portion 18c that is exposed. Typically, this exposed portion is placed against the patient during an injection. Thus, fluid ejection assembly 18 may be designed such that only the replaceable fluid ejection assembly 18 and no portion of needle-free injection assembly 14 makes contact with the patient during an injection.

Figure 2:
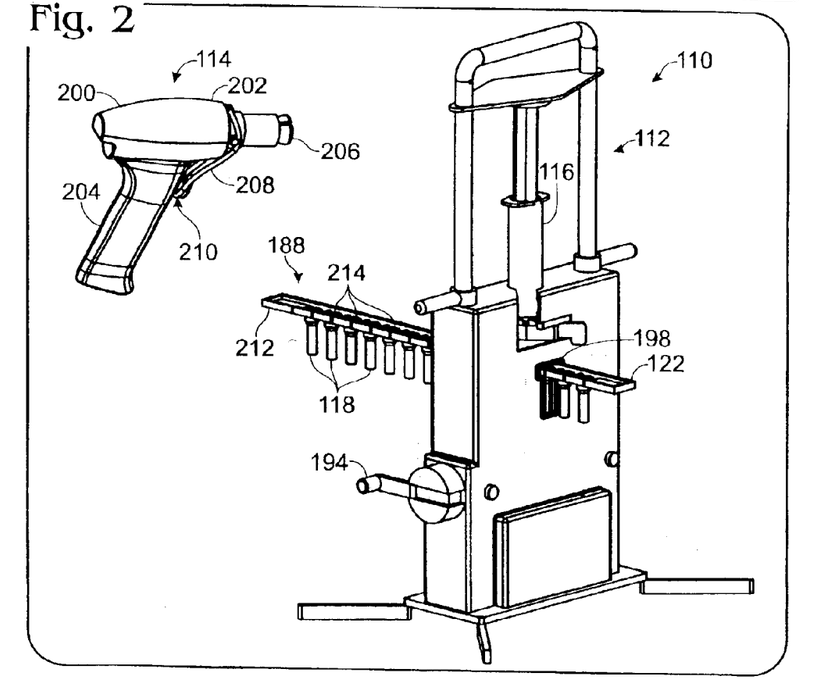
FIG. 2 is an isometric view of an embodiment of a high throughput needle-free injection system according to the present invention.

An exemplary high throughput needle-free injection system 110 is shown in FIG. 2. As shown, system 110 includes a filling station 112 and a reusable needle-free injector 114. In system 110, filling station 112 is adapted to sterilely transfer a predetermined amount of injectate from a fluid reservoir, which in the embodiment shown takes the form of a syringe 116, to a plurality of disposable cartridges 118. As shown, a cartridge rack 122 joins the plurality of disposable cartridges together.

Figure 3:
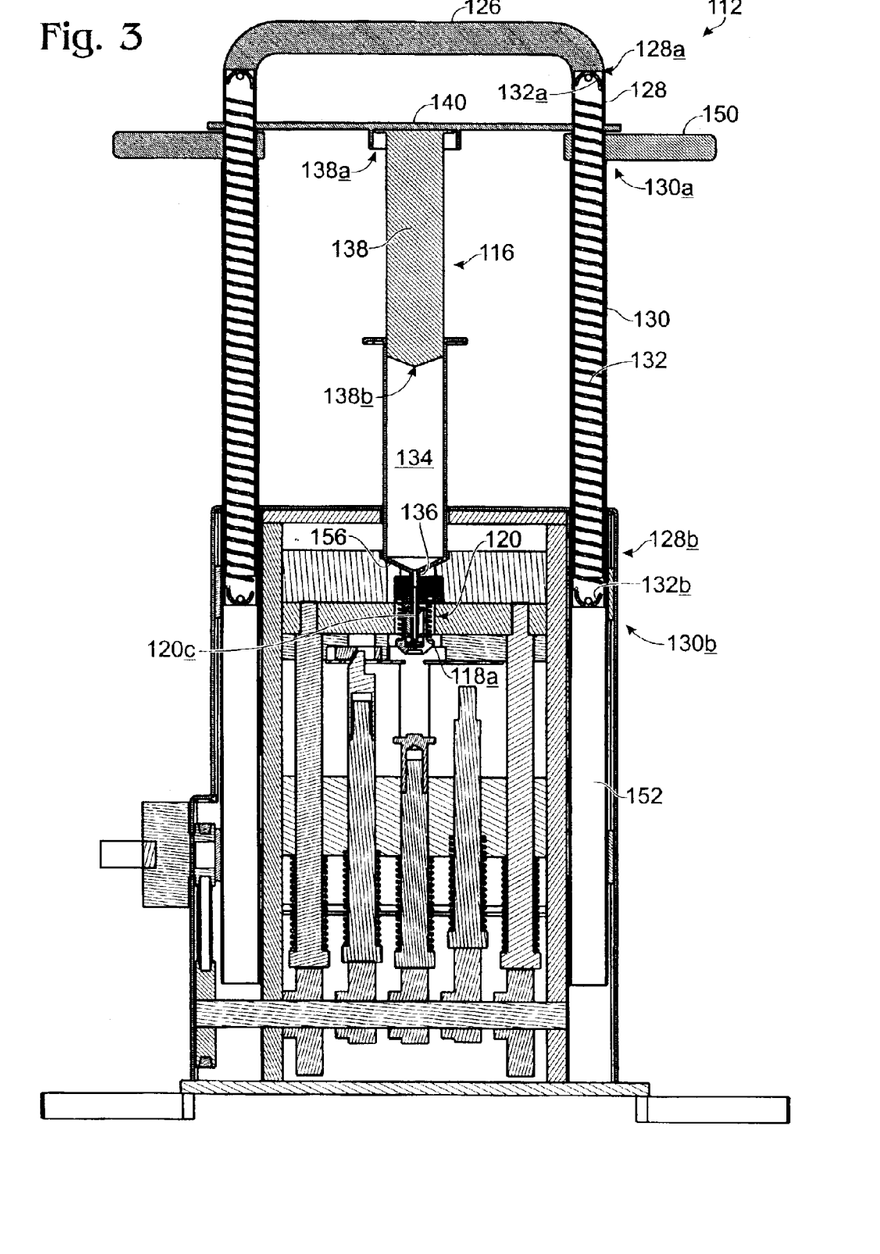
FIG. 3 is sectional side elevation view of the filling station shown in FIG. 2 showing the syringe installed but not pressurized.

FIG. 3 is a cross-section of portable filling station 112 during the setup process. As shown, filling station 112 includes syringe 116, a filler valve 120, a curved handle 126, tubular rods 128, sliding rods 130, and springs 132.

Syringe 116 includes a syringe reservoir 134 terminating in a nozzle 136 through which fluid in the syringe may be expelled. Syringe 116 further includes a plunger 138 having a first end 138a that terminates in a thumbpad 140 and a second end 138b that is received by syringe reservoir 134. Syringe 116 may be a commercially available syringe, such as the BD™ syringe, available from Becton, Dickinson and Company or other syringes such as those sold by Monoject, and Terumo. Typically, syringe 116 is able to store enough injectate to fill a number of cartridges. It should be appreciated that the size and capacity of syringe 116 may depend on availability, the size of filling station 112, the number of cartridges it is desired to fill, the shelf life of the injectate, and other relevant factors. As a non-limiting example, syringe 116 may take the form of a 60 cc syringe. However, it should be appreciated that other sizes and other types of non-syringe fluid reservoirs may be used with the present invention.

Figures 4, 5, 7:
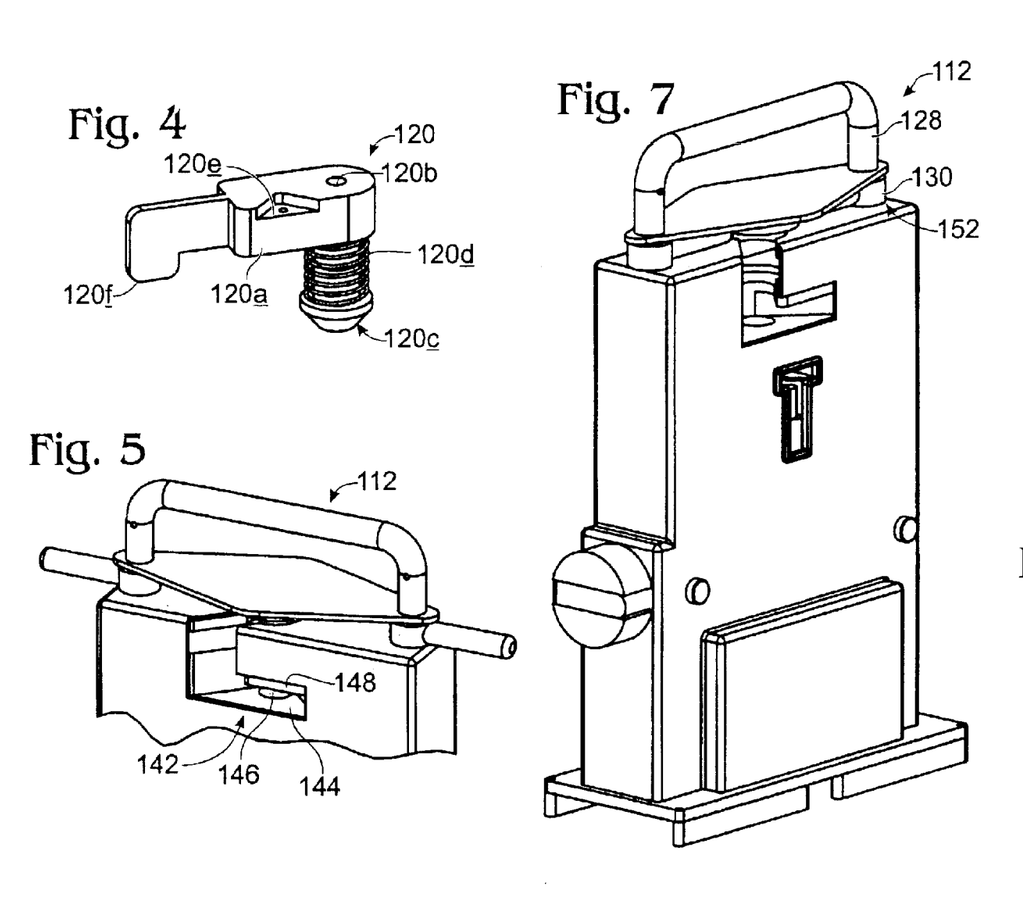
FIG. 4 is an isometric view of the filler valve shown in FIG. 2.
FIG. 5 is an isometric close-up view of the portion of the filling station shown in FIG. 2 that is adapted to receive the filler valve shown in FIG. 4.
FIG. 7 is an isometric view of the filling station shown in FIG. 2 in a storage configuration.

As previously stated, filler valve 120 provides a fluid path between syringe 116 and each of the cartridges during the filling process. FIG. 4 shows an exemplary filler valve 120. As shown, valve 120 includes a body 120a including a fluid path defined by aperture 120b. Valve 120 further includes an extended portion 120c including a spring 120d. Valve 120 also includes a recess 120e and a handle 120f, which coordinate to facilitate the positioning of the valve in station 112.

FIG. 5 is a close up of the portion of station 112 adapted to receive filler valve 120. As shown, station 112 includes a valve seat 142. Valve seat 142 includes a shelf 144 that provides access to an orifice 146. Orifice 146 is adapted to receive extended portion 120c of filler valve 120. Filler valve 120 slides into shelf 144 and may then be pushed downward, such that orifice 146 receives extended portion 120c. Filler valve 120 may then be locked into place by rotating handle 120f under ledge 148. Filler valve 120 may be removed and sterilized or disposed of and replaced as desired in order to maintain the desired level of sterility during the filling procedure. Of course it should be appreciated that alternative shapes and arrangements for filling valve 120 may be used.

It will be appreciated that in the embodiment described above, the entire fluid path consists of syringe 116, filler valve 120, and cartridges 118. Thus, any injectate introduced into the system makes contact only with syringe 116, filler valve 120, and cartridges 118. It should further be appreciated that each of these components may be disposable. In some cases, syringe 116 and each cartridge 118 may be "single use," i.e., used once and then thrown away. Because a single-use filler valve may not be practical, it may be desirable to use filler valve 120 for a given period of time, for example, several hours, half a day, or a day before being disposed of. Alternatively filler valve 120 may be used to fill a certain number of cartridges, for example, 50, 100, or 500 and then disposed of.

Returning to FIG. 3, curved handle 126 is connected at either end to a pair of tubular rods 128. Each tubular rod 128 includes a first end 128a and a second end 128b, which is adapted to engage and be received by sliding rod 130. Each sliding rod 130 includes a first end 130a and a second end 130b. A handle 150 is situated on or near first end 130a of each sliding rod 130. Each sliding rod 130 is adapted to engage and slide into a cavity 152. Thus, sliding rods 130 move relative to tubular rods 128 and cavity 152 in a manner similar to the movement of a trombone slide.

A spring 132 is housed in each tubular rod 128. Spring 132 includes a first end 132a and a second end 132b. First end 132a of spring 132 is attached to first end 128a of tubular rods 128. Second end 132b of spring 132 is attached to second end 130b of sliding rods 130. When sliding rod 130 is in the "up" position, as depicted in FIG. 3, springs 132 may be relaxed, but preferably will have some tension in them.

Syringe seat 156 is shaped to complement the external contour of the lower end of syringe 116. When the syringe is properly positioned in syringe seat 156, syringe nozzle 136 contacts aperture 120b of filling valve 120. In this position, plate 158 rests on thumbpad 140 of plunger 138.

Figure 6:
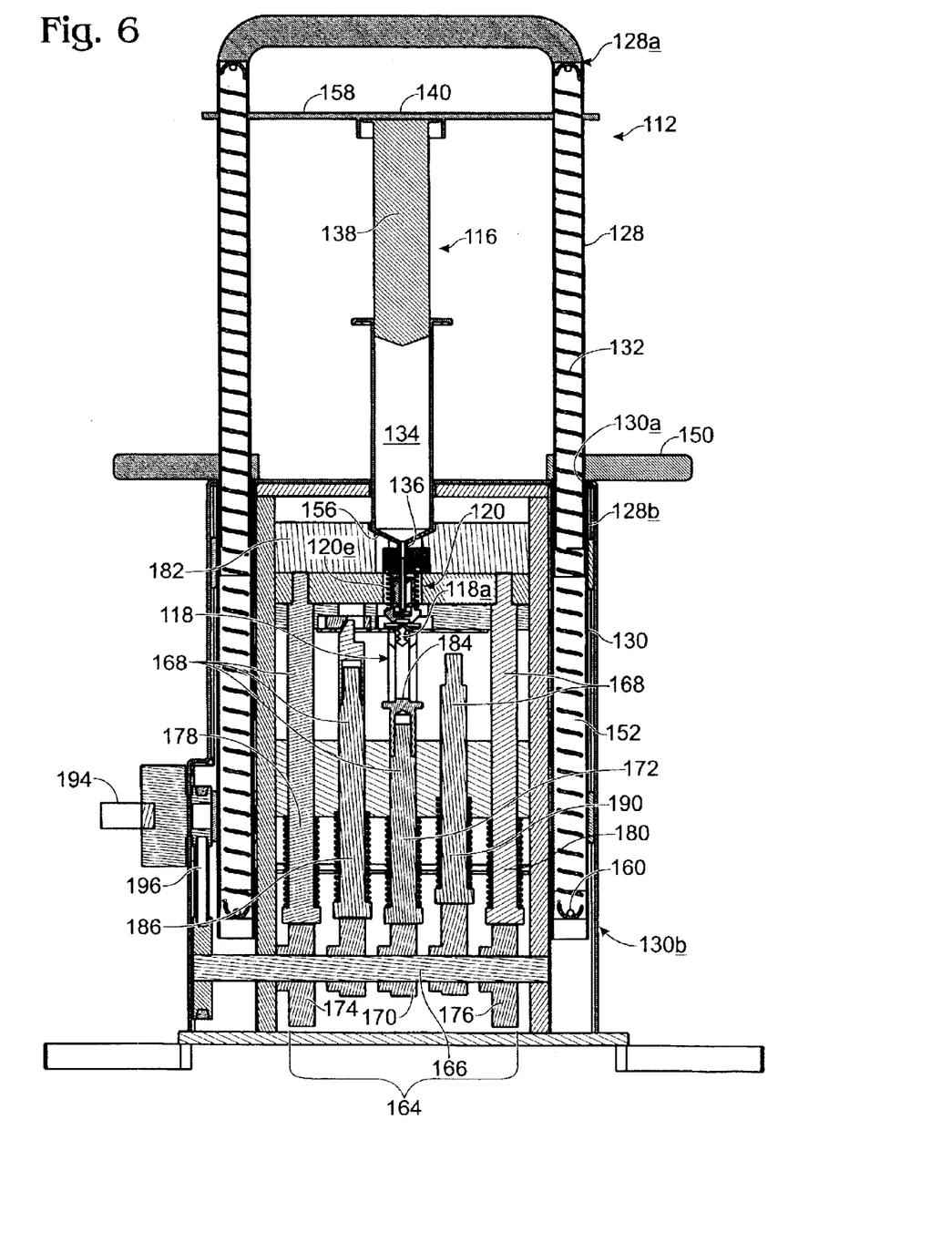
FIG. 6 is a sectional side elevation view of the filling station shown in FIG. 5 showing the syringe pressurized and the cartridge ready to be filled.

FIG. 6 depicts a filling station 112 during the filling process. As shown, handles 150 have been pushed downward, pushing sliding rods 130 into cavity 152, extending springs 132. Typically, cavity 152 will include some type of mechanism to retain second end 132b of spring 132. For example, second end 132a of spring 132 may include a detent 160 that may be retained by an orifice (not shown) located at the bottom of cavity 152. It should be appreciated that the retention mechanism may not be applied to the spring, but may instead be applied to second end 130b of sliding rods 130, to which second end 132b of spring 132 is attached.

When extended, spring 132 is biased to pull first end 128a of tubular rod 128 toward second end 130b of sliding rod 130. Because plate 158 is affixed to tubular rod 128, this bias essentially creates a downward force on plate 158. This downward force is applied by plate 158 on thumbpad 140 of plunger 138. Thus, as the contents of syringe 116 are released into the cartridges (i.e. as the cartridges are filled) the downward force on plunger 138 pushes plunger 138 further into syringe reservoir 134 until it meets resistance from liquid injectate inside the syringe reservoir. Put briefly, the force created by extended spring 132 is transmitted to syringe 116, so that the internal contents of syringe 116 are placed under constant pressure.

Filling station 112 includes a series of cams 164 attached to a rotating shaft 166. Each cam 164 is associated with a spring-loaded pin 168. Center cam 170 controls central pin 172, which is responsible for positioning and retaining cartridge 118 against the opening of filler valve 120. External cams 174 and 176 control external pins 178 and 180, respectively, which are affixed to block 182.

Rotation of shaft 166 after cartridge 118 is positioned against filler valve 120 results in a slight downward movement of pins 178 and 180 and a corresponding slight downward movement of block 182. Downward movement of block 182 compresses spring 120d on filling valve 120, opening the valve.

Figure 10:
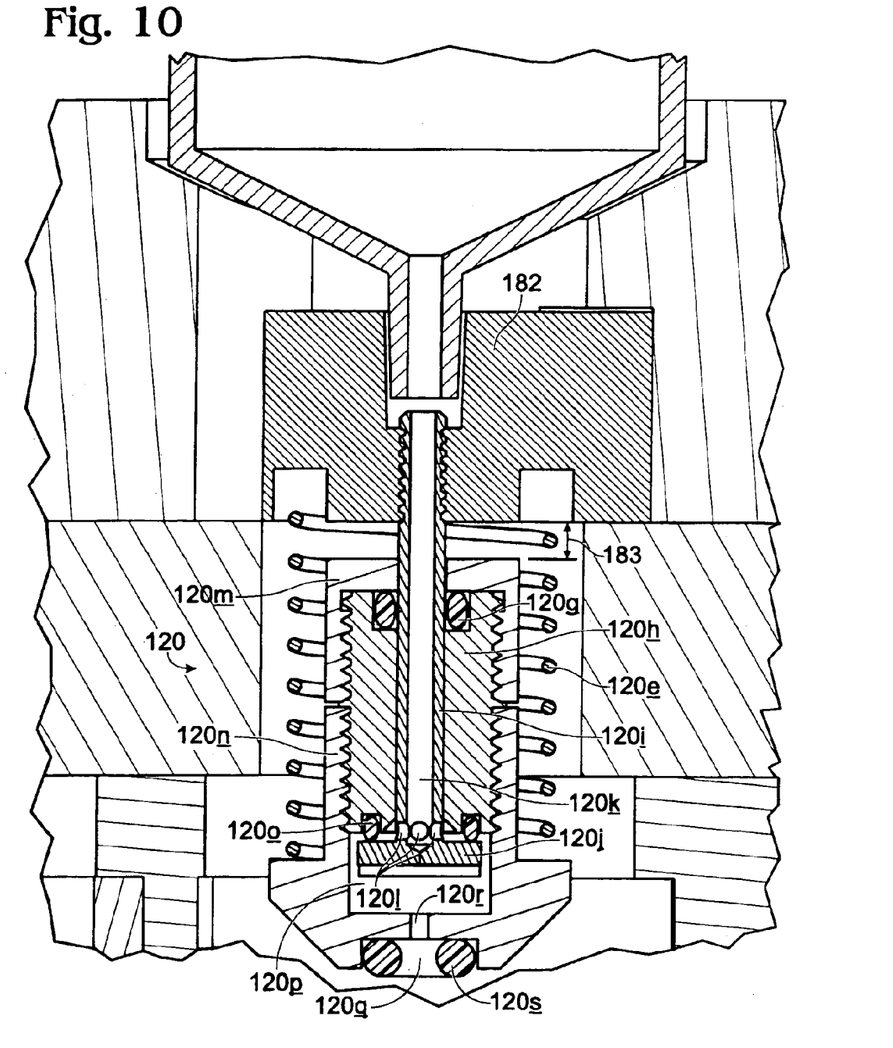
FIG. 10 is a close up of the filler valve of FIG. 6 in a closed position.
Figure 11:
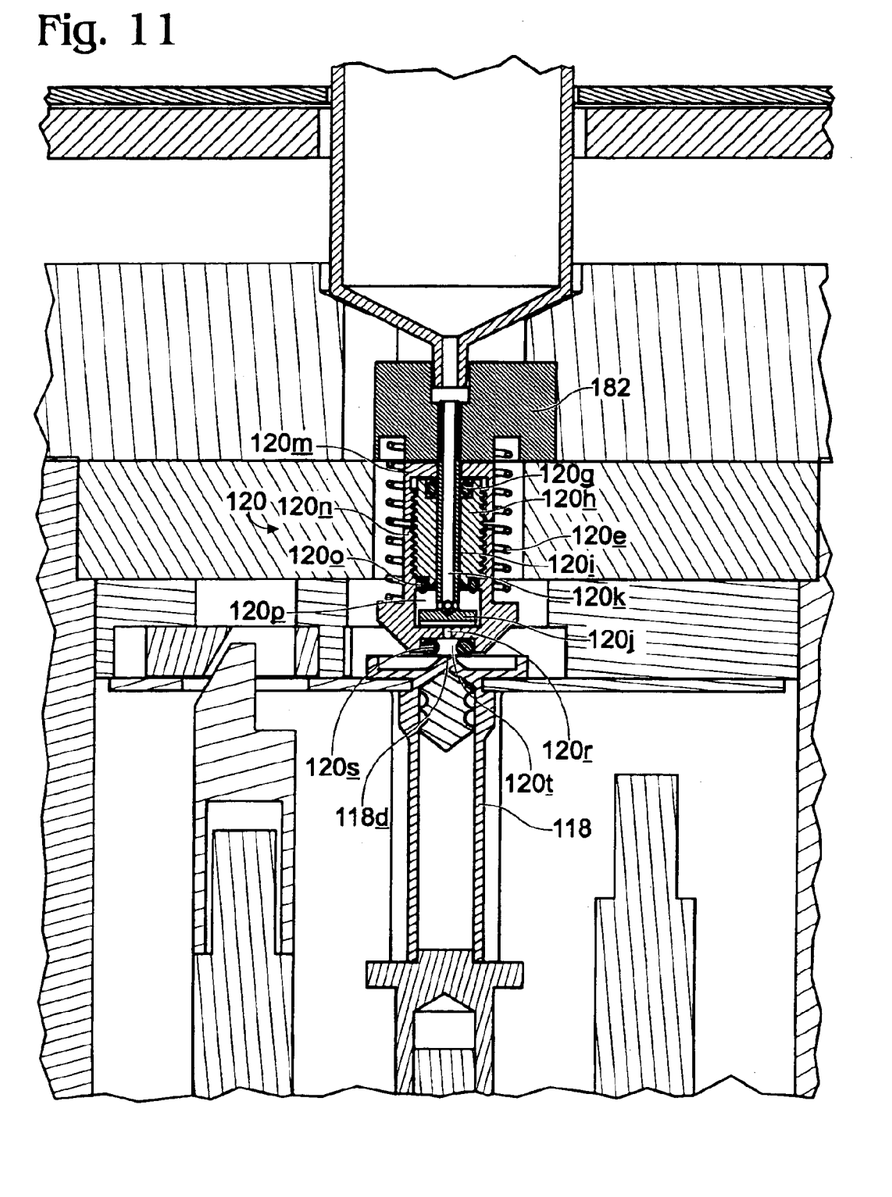
FIG. 11 is a close up of the filler valve of FIG. 6 in an open position.

FIGS. 10 and 11 show a close up of the portion of filling station 112 housing valve 120 when the valve is in closed (FIG. 10) and open (FIG. 11) positions. As shown in FIGS. 10 and 11, valve 120 further includes an o-ring 120g, which forms a seal between a middle portion 120h and a central plunger 120i, which terminates in a plug 120j. As shown, central plunger 120i defines a fluid path or channel 120k, which terminates in side channels 120l. Middle portion 120h is in a toothed engagement with upper external portion 120m and lower external portion 120n. An o-ring 120o extends from the bottom of middle portion 120h and in FIG. 10 creates a seal between middle portion 120h and plug 120j. Plug 120j resides in a chamber 120p, which is fluidly connected to chamber 120q via channel 120r. An o-ring 120s extends from the bottom of lower external portion 120n and is housed within opening 120q.

In FIG. 10, no cartridge is seated beneath filler valve 120 and valve 120 is closed. In this configuration, spring 120e is extended and a gap 183 exists between block 182 and upper external portion 120*m*. As shown, plug 120*j* contacts o-ring 120*o*, preventing any liquid injectate in channel 120*k* from escaping into chamber 120*p*.

In FIG. 11, a cartridge 118 is seated directly beneath filler valve 120 such that aperture 118*d* is in contact with o-ring 120*s*, creating a sealed chamber 120*t* from opening 120*q*. As shown, block 182 has moved downwards and is in contact with the upper surface of filler valve 120. This movement compresses spring 120*e* and pushed plunger 120*k* downward, releasing plug 120*j* from contact with o-ring 120*o*. Thus, liquid injectate in channel 120*k* is released through side channels 120*l* and into chamber 120*p*. Once liquid injectate is in chamber 120*p*, it can flow through channel 120*r*, past o-ring 120*s* and into chamber 120*t* and then into cartridge 118 via aperture 118*d*.

Thus, the opening of valve 120 allows fluid in syringe 116 to flow into cartridge 118. As cartridge 118 fills with fluid, a plunger 118*a* within cartridge 118 is pushed downwards to the bottom of the cartridge. When cartridge 118 is full, plunger 118*a* meets end 184 of central pin 172. Once the cartridge is filled, pin 186 acts as a cog, moving cartridge rack 122 through the filling station until positioning pin 190 properly positions the next empty cartridge in the filling station.

Typically, filling device 112 includes a power generator to control operation of the device. It will be appreciated that the power generator may be a user, motor, pump, or other mechanism.

For example, as described above, movement of pins 172, 178, 180, 186 and 190 is controlled and powered by rotation of shaft 166. Rotation of shaft 166 may be electronic, motor-driven, hand-driven, or the like. If rotation of shaft 166 is hand-driven, filling station 112 may include a hand crank 194 (also shown in FIG. 2). In the depicted embodiment, movement of hand crank 194 rotates belt 196, which engages and thus rotates shaft 166. Thus, in this embodiment, the power generator includes a user operating a hand crank.

Turning briefly to FIG. 7, filling device 12 may be configured to adopt a compact storage configuration. FIG. 7 shows a storage configuration that may be adopted by filling station 112. As shown, syringe 116 has been removed and tubular rods 128 and sliding rods 130 are pushed into cavity 152. This storage configuration reduces the amount of space required when the device is not in use and enables the device to be easily transported.

Figure 8:
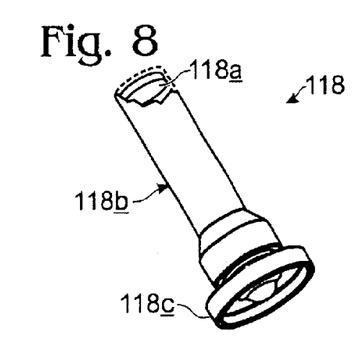
FIG. 8 is an isometric view of the cartridge shown in FIG. 2.

FIG. 8 is a close-up view of a single cartridge 118. It can be seen that each cartridge 118 includes plunger 118*a* disposed within a shaft 118*b*. Shaft 118*b* terminates in a nozzle 118*c*. Typically, it is shaft 118*b*, or a portion thereof, that is received or otherwise engaged by injector 114 in preparation for an injection. Nozzle 118*c* may include one or more orifices (not shown) through which injectate in the cartridge may be released. Typically, nozzle 118*c* is exposed when the injector engages shaft 118*b* so that the head of nozzle 118*c* may be placed against the patient during injection. In this manner, only the removable cartridge, and not the injector, makes contact with the patient. Thus, when the cartridge is removed and replaced between injections, the injector may be reused without risk of contamination between patients.

It should be appreciated that it may be desirable for cartridge 118 to be a single use or disposable cartridge that, once spent, cannot be reused. Consequently, it will be appreciated that some materials are more useful for disposable cartridges. For example, plastics, which are lightweight and inexpensive, tend to be suitable for disposable applications.

Returning to FIG. 2, it can be seen that multiple cartridges 118 are joined by a rack structure 122, forming a rack assembly 188. In the embodiment shown, rack assembly 188 is fed through filling station 112 via opening 198. As described above, during the filling process, reservoir 116 is fluidly connected to each cartridge 118 via a filler valve 120. As shown, the orientation of rack assembly 188, as it is fed through the filling station, is such that the nozzle end 118*c* of each cartridge 118 is presented to filler valve 120. However, it should be appreciated that alternative configurations may be used.

Figure 9:
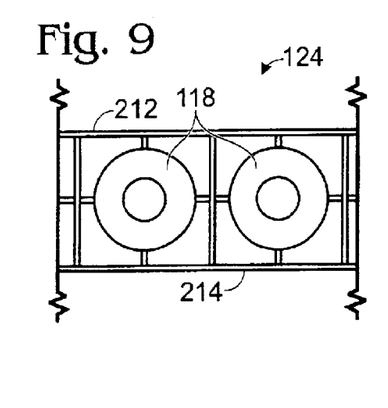
FIG. 9 is a schematic bottom view of the rack structure shown in FIG. 2.

As shown in FIG. 9, rack structure 122 is formed of plastic and each cartridge 118 is joined to the external frame 212 of the rack structure by several sprues 214. Thus, the entire rack assembly 188 including the cartridges may be extruded as a single piece. Alternatively, the cartridges can be formed separately and then joined to the rack structure using any suitable means. Cartridge 118 can be released from rack structure 122 by breaking the sprues away from the cartridge. In system 110, filling station 112 is adapted to receive and fill only cartridges that are part of a rack assembly. As such, once a cartridge is broken away from the rack structure, it cannot be refilled. Of course, it will be appreciated that a filling station could be adapted to receive single cartridges or rack assemblies having different configurations from those shown.

Returning to FIG. 2, in the embodiment shown, needle-free injector 114 includes a generally gun-shaped body 200 having a barrel portion 202 and a handgrip portion 204. Barrel portion 202 houses the propulsion assembly and terminates in a chuck 206, which is controlled by lever 208. As shown, lever 208 is designed to be within easy reach of a user holding injector 114 by handgrip portion 204. Handgrip portion 204 further includes trigger 210, which controls activation of the propulsion assembly. Of course it will be appreciated that needle-free injector need not be gun-shaped. Many alternative shapes are suitable for use in the present invention, including elongated tubular shapes and the like.

Those of skill in the art will be familiar with various propulsion assemblies useful for needle-free injectors. Suitable needle-free injectors include those described in U.S. Pat. Nos. 4,941,880, 5,064,413, 5,312,335, 5,383,851, 5,399,163, 5,520,639, 5,993,412, 6,096,002, 6,264,629, 6,383,168, 6,471,669, and co-pending U.S. Ser. No. 10/164, 920, each of which is hereby incorporated by reference in its entirety for all purposes.

Generally, the propulsion assembly is adapted to engage cartridge 118 and directly or indirectly advance plunger 118*a* towards nozzle end 118*c*. The movement of plunger 118*a* should expel liquid injectate in cartridge 118 from nozzle 118*c* with sufficient pressure to allow the fluid to penetrate the target, such as the dermal layers of a patient's skin, to the desired degree. As stated above, trigger 210 typically controls activation of the propulsion assembly. However, it should be appreciated that other controllers could be used, including user-activated buttons, touch pads, levers or the like.

Chuck 206 is adapted to removably engage a filled cartridge 118 such that a nozzle end 118*c* of the cartridge 118 is presented for placement against the patient. Pulling lever 200 towards grip 202 opens chuck 204 so that the shaft 118*u* of filled cartridge 118 may be partially inserted into the barrel portion 202. Lever 200 may then be pushed forward to lock the cartridge into place. After an injection, lever 200 may once again be pulled backwards to open chuck 202 and release the spent cartridge.

CONCLUSION

The present invention provides a system and apparatus for high throughput needle-free injections. It is believed that the disclosure set forth above encompasses multiple distinct inventions with independent utility. While each of these inventions has been disclosed in its preferred form, the specific embodiments thereof as disclosed and illustrated herein are not to be considered in a limiting sense, as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

What is claimed is:

1. A needle free injection system comprising:
   an injection assembly comprising:
      a single-use removable fluid ejection assembly comprising:
         a body terminating in a nozzle;
         a fluid reservoir housed within the body, the fluid reservoir being adapted to receive a fluid injectate; and
         a plunger disposed within the fluid reservoir;
      a propulsion assembly comprising:
         a housing adapted to receive at least a portion of the removable fluid ejection assembly; and
         a propulsion system adapted to apply sufficient force to the fluid ejection assembly to cause ejection of the fluid injectate through the nozzle; and
   a filling device adapted to sterilely deliver a predetermined amount of injectate from a common reservoir to a plurality of fluid ejection assemblies, the filling device comprising:
      a filler valve including:
         a fluid path disposed between the common reservoir and the single use removable fluid ejection assembly;
         a valve seat for receiving the filler valve;
         a rack for receiving the plurality of fluid ejection assemblies; and
      means for sealing and permitting fluid to sterilely flow under pressure from the common reservoir into the fluid ejection assembly without insertion of any component of the filler valve into the fluid ejection assembly.

2. The injection system of claim 1 wherein the rack is linear.

3. The injection system of claim 2 wherein the rack comprises a single file line of a plurality of fluid ejection assemblies.

4. The injection system of claim 3 wherein the seal means includes a resilient member that is positioned on the fluid ejection assembly adjacent the nozzle.

5. The injection system of claim 4 wherein the resilient member comprises an O-ring.

6. The injection system of claim 1 wherein the common reservoir is disposable.

7. The injection system of claim 1 wherein the fluid path is disposable.

8. The needle free injection system of claim 1, wherein the common reservoir is a syringe including an elongate tube, a plunger and a nozzle, and the filler valve includes:
   a body having a syringe seat configured to receive a portion of the syringe including the nozzle and situate the syringe so that a portion of the syringe extends upwards, away from the body; and
   a biasing mechanism extending upwards, away from the body, and configured to place constant pressure on the syringe plunger.

9. The needle free injection system of claim 8, wherein the biasing mechanism includes a U-shaped member having a bridge and a pair of legs extending from the bridge, and wherein the body includes a pair of apertures into which the legs of the U-shaped member may be slidingly received, the U-shaped member being situated such that when a syringe is seated in the syringe seat, the movement of the legs of the U-shaped member into the apertures results in movement of the plunger further into the elongate tube.

10. The needle free injection system of claim 9, further comprising a spring disposed between the body and the U-shaped member.

11. The needle free injection system of claim 1, wherein the filler valve further includes:
   a shaft;
   a plurality of cams in mechanical relationship with the shaft; and
   a plurality of pins in mechanical relationship with the cams.

12. The needle free injection system of claim 11, wherein, upon rotation of the shaft, a first pin is able to engage a fluid ejection assembly within the rack, and temporarily position the fluid ejection assembly against a valve retained within the valve seat.

13. The system of claim 12, wherein, upon rotation of the shaft, a second pin is able to temporarily engage the rack and advance the rack until the first pin positions the fluid ejection assembly.

14. A needle free injection system comprising:
   an injection assembly comprising:
      a single-use removable fluid ejection assembly comprising:
         a body terminating in a nozzle;
         a fluid reservoir housed within the body, the fluid reservoir being adapted to receive a fluid injectate; and
         a plunger disposed within the fluid reservoir;
      a propulsion assembly comprising:
         a housing adapted to receive at least a portion of the removable fluid ejection assembly; and
         a propulsion system adapted to apply sufficient force to the fluid ejection assembly to cause ejection of the fluid injectate through the nozzle; and a filling device adapted to sterilely deliver a predetermined amount of injectate from a common reservoir to a plurality of fluid ejection assemblies, filling device comprising:
   a filler valve including:
      a fluid path disposed between the common reservoir and the syringe use removable fluid ejection assembly;
      a valve seat for receiving the filler valve;
      a rack for receiving the plurality of fluid ejection assemblies; and
a seal for guiding fluid into the fluid ejection assembly without insertion of any component of the filler valve into the fluid ejection assembly,
wherein the filling device is actuated by hand such that the injection of fluid under pressure moves the plunger and results in the rack being indexed to position another fluid ejection assembly for filling.

15. The injection system of claim 14 wherein the rack is linear.

16. The injection system of claim 15, wherein the rack comprises a single file line of a plurality of fluid ejection assemblies.

17. The injection system of claim 15, further comprising a cog for indexing the linear rack to position another fluid ejection assembly for filling.

18. The injection system of claim 14, wherein the seal comprises seal means for permitting fluid to sterilely flow under pressure from the common reservoir into the fluid ejection assembly.

19. The injection system of claim 14 wherein the common reservoir is disposable.

20. The injection system of claim 14 wherein the fluid path is disposable.

21. The needle free injection system of claim 14, wherein the common reservoir is a syringe including an elongate tube, a plunger and a nozzle, and the filler valve includes:
   a body having a syringe seat configured to receive a portion of the syringe including the nozzle and situate the syringe so that a portion of the syringe extends upwards, away from the body; and
   a biasing mechanism extending upwards, away from the body, and configured to place constant pressure on the syringe plunger.

22. The needle free injection system of claim 21, wherein the biasing mechanism includes a U-shaped member having a bridge and a pair of legs extending from the bridge, and wherein the body includes a pair of apertures into which the legs of the U-shaped member may be slidingly received, the U-shaped member being situated such that when a syringe is seated in the syringe seat, the movement of the legs of the U-shaped member into the apertures results in movement of the plunger further into the elongate tube.

23. The needle free injection system of claim 21, further comprising a spring disposed between the body and the U-shaped member.

24. The needle free injection system of claim 14, wherein the common reservoir is a syringe including an elongate tube, a plunger and a nozzle, and the filler valve includes:
   a body having a syringe seat configured to receive a portion of the syringe including the nozzle and situate the syringe so that a portion of the syringe extends upwards, away from the body; and
   a biasing mechanism extending upwards, away from the body, and configured to place constant pressure on the syringe plunger.

25. The needle free injection system of claim 14, wherein the filler valve further includes:
   a shaft;
   a plurality of cams in mechanical relationship with the shaft; and
   a plurality of pins in mechanical relationship with the cams.

26. The needle free injection system of claim 25, wherein, upon rotation of the shaft, a first pin is able to engage a fluid ejection assembly within the rack, and temporarily position the fluid ejection assembly against a valve retained within the valve seat.

27. The system of claim 26, wherein, upon rotation of the shaft, a second pin is able to temporarily engage the rack and advance the rack until the first pin positions the fluid ejection assembly.

* * * * *